United States Patent [19]

Dodge

[11] 4,085,751
[45] Apr. 25, 1978

[54] DRAINAGE APPARATUS

[75] Inventor: Larry H. Dodge, St. Charles, Mo.

[73] Assignee: Sherwood Medical Industries Inc., St. Louis, Mo.

[21] Appl. No.: 619,109

[22] Filed: Oct. 2, 1975

[51] Int. Cl.² .................. G01F 19/00; A61B 5/00
[52] U.S. Cl. ................................. 128/275; 128/276
[58] Field of Search ............... 128/2 F, 275, 276; 141/59

[56] References Cited

U.S. PATENT DOCUMENTS

| | | | |
|---|---|---|---|
| 2,936,757 | 5/1960 | Trace | 128/276 |
| 3,180,376 | 4/1965 | Sanborn | 141/59 |
| 3,545,440 | 12/1970 | Roslyn et al. | 128/276 |
| 3,699,815 | 10/1972 | Holbrook | 128/276 |

*Primary Examiner*—Hugh R. Chamblee
*Assistant Examiner*—Robert F. Cutting
*Attorney, Agent, or Firm*—S. N. Garber; W. R. O'Meara

[57] ABSTRACT

A thoracic drainage device including a rigid container having a drainage collection chamber and a liquid seal chamber centered above the collection chamber. A tube adapted for connection with the pleural cavity of a patient is connected to the lid of the device and extends into the liquid seal chamber to a point below the level of an initial amount of liquid provided therein. The liquid seal chamber has a relatively small height relative to its length and width so that it contains a relatively large amount of liquid of shallow depth. The seal chamber has an upper wall with a central opening for the flow of liquid through the opening and into the collection chamber, the upper wall preventing or reducing the flow of liquid out of the liqud seal chamber due to an inadvertent tipping of the device or sloshing during movement from one location to another.

25 Claims, 3 Drawing Figures

DRAINAGE APPARATUS

BACKGROUND OF THE INVENTION

This invention relates to drainage apparatus and more particularly to a drainage device for draining fluids from a body cavity.

Drainage devices, such as thoracic drainage devices utilizing drainage bottles or chambers, are initially partially filled with a liquid such as water or a saline solution, to a level slightly above the bottom wall of the chamber. A tube or the like is used which extends through the upper wall and downwardly through the chamber with the lower end or outlet of the tube below the water level to provide the necessary underwater or liquid seal. A main disadvantage of this construction is that, as the level of drainage liquid rises above the lower end of the tube, the force necessary to expel liquid from the tube and fluid from the pleural cavity increases due to the increasing pressure head above the tube outlet thus making it increasingly difficult for the patient to expel fluid. In order to avoid this increasing liquid head, the tube may be adjusted by raising it as the liquid rises in the collection chamber. However, this requires continuous maintenance on the part of personnel.

In U.S. Pat. No. 3,545,440, a float member is connected to the bottom of a flexible drainage tube so that the lower end of the tube tends to maintain the liquid head substantially constant as the drainage liquid rises in the chamber. This latter arrangement, however, results in a relatively complicated and expensive structure. Another method of maintaining a constant head is to connect the chamber to a vacuum source instead of to atmosphere and manually vary the negative pressure applied as the liquid head increases. This latter method, of course, is also complicated and requires continuous monitoring.

In U.S. Pat. No. 2,936,757, a flexible bag having a pocket formed therein receives a drainage tube so that drainage flows into the liquid in the pocket which forms a liquid seal and then, as the pocket overflows, the liquid fills the main drainage collection chamber. This construction has certain disadvantages, for example, the bag is flexible and changes volume with changes in internal or external pressures. For example, when the pleural cavity off the patient has a negative pressure or if a suction force is applied to assist the drainage flow, the bag tends to collapse. Also, any tipping of the bag would tend to move the relatively small quantity of liquid out of the pocket which forms the liquid seal so that there is danger of breaking the liquid seal and allowing air to reach the interior of the drainage tube and pleural cavity. Also, where the liquid seal is of a relatively low volume, the occurrence of high negative pressures in the cavity, such as may occassionally occur during heavy gasping, may draw a sufficient amount of liquid into the drainage tube to cause the liquid seal to be broken.

SUMMARY OF THE INVENTION

It is therefore an object of the present invention to provide an improved drainage device which substantially avoids the above-mentioned undesirable features.

In accordance with one form of the present invention, a container is provided which has a liquid seal chamber centered above a drainage liquid collection chamber, and fluid passage means adapted for connection with a body cavity communicates with the seal and collection chambers. In accordance with another form of the invention, a container is provided which has a collection chamber and a liquid seal chamber above the collection chamber with the liquid seal chamber having side walls and an upper wall extending radially inwardly from the side walls. In accordance with another aspect of the invention, a relatively rigid container is provided which has a liquid seal chamber above a drainage collection chamber with the liquid seal chamber dimensioned to have a length and width greater than its height.

These, as well as other objects and advantages of the present invention will become apparent from the following detailed description and accompanying drawing.

DESCRIPTION OF THE PREFERRED EMBODIMENT

Figure 1:
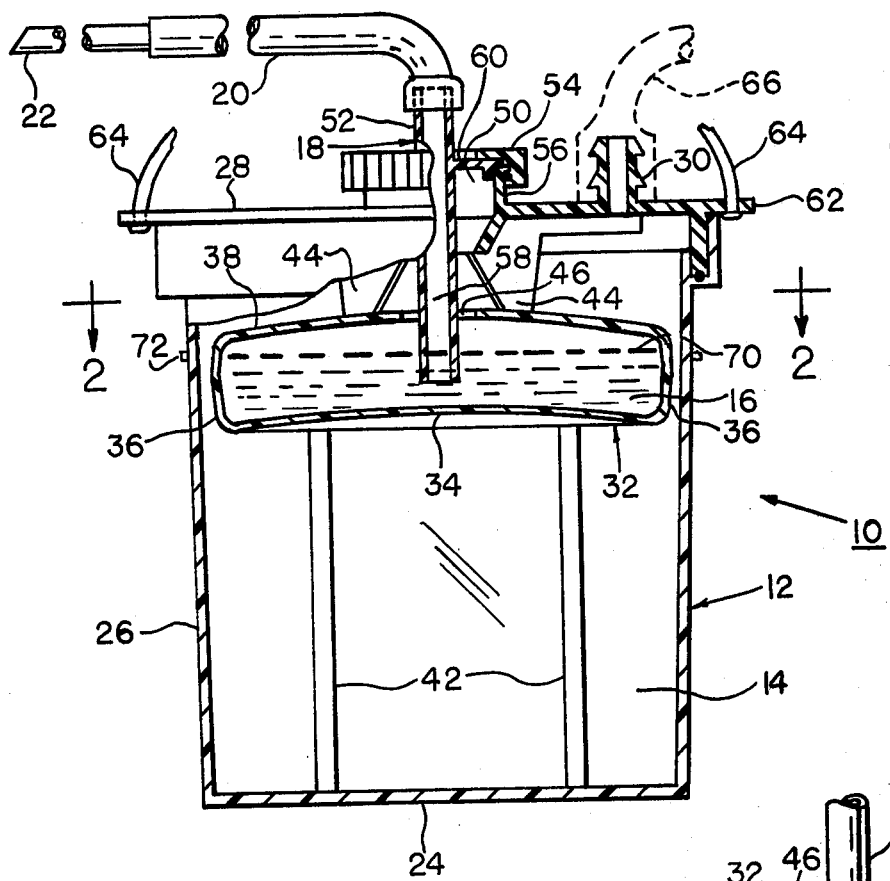
FIG. 1 is an elevational cross-sectional view of a thoracic drainage device in accordance with a preferred embodiment of the invention.
Figure 2:
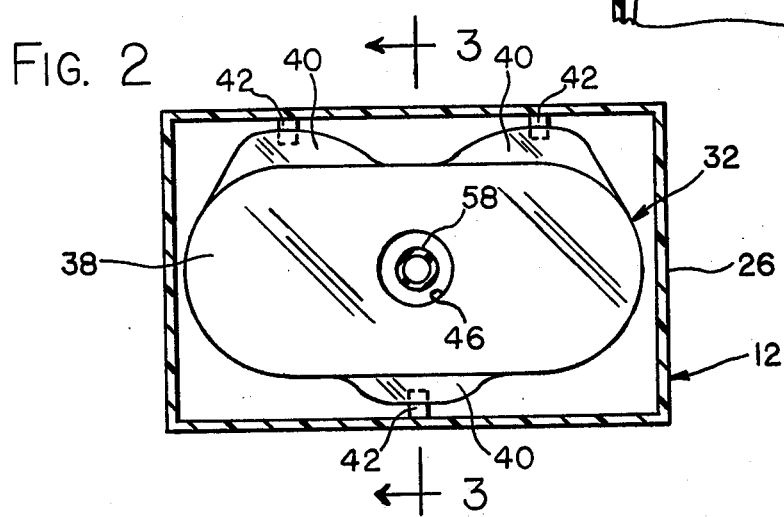
FIG. 2 is a cross-sectional view taken along line 2—2 of FIG. 1.

Referring now to the drawing, and particularly to FIG. 1, there is shown a thoracic drainage device 10 including a container 12 having a fluid drainage collection chamber 14 and a liquid seal chamber 16 above the collection chamber. A drainage fluid inlet member 18 communicating with the interior of the container is shown connected by a tube 20 to a catheter 22 that is adapted for insertion into the pleural or thoracic cavity of a patient to be drained. The container 12 has a bottom wall 24 and four vertically extending side walls 26 formed integrally with the bottom wall, the container being generally rectangular in cross-section as seen in FIG. 2 although it may be elliptical to avoid corners where desired. The container 12 has an upper open end which is closed by a cover or lid 28 carrying the fluid inlet member 18 and having a gas outlet 30.

Figure 3:
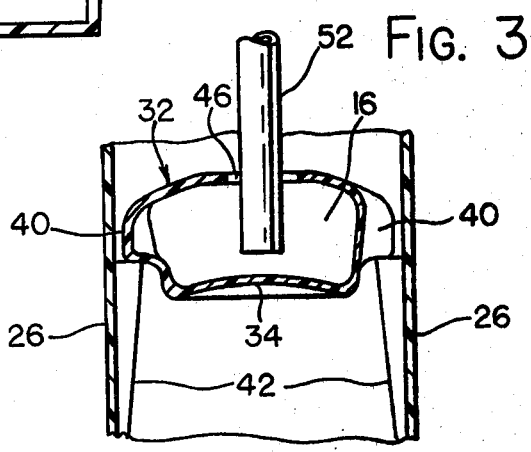
FIG. 3 is a cross-sectional view taken along line 3—3 of FIG. 2.

The liquid seal chamber 16 is preferably in the form of a separate container 32 having a bottom wall 34, peripheral side walls 36, and an upper wall or cover 38, all of these walls being shown as integrally formed. The container 32 may be formed by any suitable method, for example, by blow molding. The liquid seal container 32 is positioned within the interior of container 12 before the lid 28 is attached to the container. Referring also to FIGS. 2 and 3, the liquid seal container 32 is shown formed with three radially outwardly extending flanges 40 which respectively engage three supporting ribs 42 integrally formed on the interior of container 12. The lid 28 is provided with a plurality of circumferentially spaced integral ribs 44 which engage the top of the container 32 to locate it in a fixed position in the upper portion of chamber 14 although other means or additional means may be employed to center and hold the container 32 in place.

Liquid seal chamber 16 is provided with an opening 46 spaced from the lower wall 34 which connects the seal chamber 16 in fluid communication with the collection chamber 14. The opening 46 is shown formed in the geometric center of the upper wall 38 in aligned relation with an entrance and fill opening 50 in the lid 28.

The drainage inlet member 18 includes a tube or passageway member 52 secured in the fill opening 50 by a closure cap 54 which receives a threaded neck 56 at the fill opening. The drainage inlet tube 52, which has a lumen 58, extends through the fill opening 50 and above the lid 28 where it connects with the tube 20. The tube 52 extends through opening 46 and into the liquid seal chamber 16 with its lower outlet end close to, but spaced above the bottom wall 34. The inlet member 18 has a radially outwardly extending annular flange 60 integral with tube 52 which provides a seal for cap 54 to seal the fill opening 50. Thus, in the illustrated embodiment of FIG. 1, the catheter 22 is connected in direct fluid communication with the seal chamber 16 so that drainage fluid flows directly into the seal chamber 16 before flowing into the collection chamber 14. The lid 28 is also shown provided with a peripheral flange 62 having holes or slots therein for receiving a supporting strap 64 which may be suspended from the patient or used for hanging the device 10 from a support.

the drainage device 10 is generally connected well below the patient so that fluid from the cavity can flow by the force of gravity into the device. In such case, the gas outlet is open to the atmosphere and serves as a gas vent. Where it is desired to employ a suction force to aid in the drainage of fluid from the cavity, the gas outlet is connected, such as by a hose or tube shown in phantom at 66, to a source of suction or negative pressure. In the latter case, the tube 66 may be connected to a controlled or regulated source of negative pressure such as another "bottle" or chamber utilizing a conventional regulating manometer of the like.

the liquid seal chamber 16 is preferably initially partially filled with a suitable liquid 70, such as a saline solution, to a predetermined level, such as indicated by indicia 72 near the top of the chamber. Indicia 72 may be, for example, a suitable marking or hump formed on container 12 or 32 or a mark on a label positioned on the side of container 12. Such label may also contain indicia or calibration marks for visually determining the amount of liquid in the chamber 14 at any given time. This initial quantity of liquid may be poured into opening 50 before the inlet member 18 and cap 54 are attached, the liquid flowing directly into the aligned opening 46 in the container 32.

The container 32 defining the seal chamber 16 is dimensioned so that there are spaces between its peripheral side walls 36 and the peripheral side walls of container 12 which provide fluid communication between the chambers 14 and 16 for the flow of drainage liquid from the patient's cavity to the collection chamber 14. The liquid seal formed by liquid 70, of course, prevents air and the migration of bacteria and the like from reaching the lumen 58 and pleural cavity of the patient while allowing gas and drainage liquid to flow from the pleural cavity into the liquid seal and then into the collection chamber 14 so that the patient retains a negative pressure in the pleural cavity for normal breathing. Gas or air from the pleural cavity flows from the catheter tube 20 into inlet tube 52, bubbles through the liquid 70, and then passes through opening 46 at the top of chamber 16 and out of the container 12 through outlet 30 to either atmosphere or to a negative source of pressure when used. Drainage liquid flows into the liquid 70 and, as the liquid seal chamber fills and overflows, drainage liquid flows out of container 32 through opening 46, over the upper wall 38, down the side walls 36, and into the drainage collection chamber 14. As is apparent from FIGS. 1 and 3, the upper side of each of the walls 34 and 38 of the chamber 16 is convex and slopes downwardly from its geometric center. In this way, solid or semi-solid discharge material does not build up near the bottom of tube 52 or at the opening 46 to block or partially block the flow of fluid.

Liquid seal chamber 16 has a relatively large volume to height ratio so that it holds a relatively large volume of liquid but produces a relatively constant and small liquid head above the bottom of the inlet tube 52. Since the level of the initial amount of liquid in chamber 16 is near the top, only a small amount of drainage liquid is required to fill the chamber before it begins to flow over the top and down into the collection chamber 14. Thus, there can be only a small change in the head above the lower end of tube 52, the head being limited by the height of the chamber. If the chamber 16 is initially completely filled, there is no change in the pressure head during operation of the device unless some liquid is lost during sloshing. The small pressure head obtained with this construction minimizes the pressure needed to expel gas from the pleural cavity. Because of the relatively large volume of liquid in chamber 16, there is less chance that the seal will be broken because of a high negative pressure being produced by the patient, such as due to heavy gasping, or due to the inadvertent tipping of the container 12.

The high volume to height ratio is obtained with the present seal chamber 16 by making the chamber relatively long and wide compared to the height of the chamber. Preferably, the length of the chamber 16 is greater than three times the height, and two times the width with the width being greater than the height. In one construction, good results were obtained by using a chamber similar in shape to the container 32 with the length, as measured from the left end to the right end in FIGS. 1 and 2, approximately four times the height and slightly greater than twice the width, the width being measured across the main portion at the opening 46 (disregarding the flange 40).

The opening 46 which has its center coincident with the vertical axes of the chambers 14 and 16, and the lumen 58, is preferably substantially smaller than the width and length of the liquid seal chamber so that inadvertent tipping, within limits, and normal handling of the drainage device 10, will not cause the liquid in the seal chamber 16 to flow out and into the drainage chamber 14 to break the liquid seal at the lower end of tube 52. Preferably, the diameter of the opening 46 is sufficiently small that, when the device 10 is tipped right or left as viewed in FIG. 1 such as by an angle of 25° from the vertical, the initial amount of liquid in chamber 16, when filled to the indicia 72, will not flow out of the opening 46. Preferably, the length of the chamber 16 is greater than four times the diameter of opening 46 while the width is greater than two times the diameter. It has been found that with these relationships, the seal chamber 16 retains its initial amount of liquid or a sufficient amount or provide an effective liquid seal at the lower end of tube 52 even after the drainage device is handled with some degree of tipping.

It should be noted that the vertical axes of symmetry of the chambers 14 and 16 are substantially coincident and substantially intersect the center of gravity of each chamber so that the weight of the liquid in the chamber tends to maintain the device 10 in a substantially balanced condition as the collection chamber fills during operation when the device is in the upright steady state condition.

The containers 12 and 32 are preferably formed of a relatively rigid transparent material, for example, a relatively hard plastic such as transparent butadiene styrene, acetate butyrate styrene or the like. With relatively hard plastic, the volumes of the chambers substantially do not vary even though the pressures inside the device may vary due to the breathing characteristics of the patient and/or changes in vacuum when a negative pressure source is used. Also, inadvertent external forces applied to the container 12 will not cause a significant compression of the chambers and this tends to avoid the possibility of drainage fluid being inadvertently returned to the patient.

It is to be understood that the foregoing description and accompanying drawing have been given only by way of illustration and example, and that alterations and changes of the present disclosure, which will be readily apparent to one skilled in the art, are contemplated as within the scope of the present invention.

What is claimed is:

1. A fluid drainage device for collecting drainage fluid from a cavity of a patient comprising a relatively rigid container having a fluid drainage collection chamber therein, a liquid seal chamber therein having a bottom wall, side walls, an upper wall extending generally radially inwardly from said side walls and spaced above said bottom wall, and an opening in said upper wall connecting said collection and seal chambers in fluid communication for the passage of fluid therebetween, gas outlet means for removing gas from the interior of said container, said seal chamber being disposed above said collection chamber with its vertical axis substantially coincident with the vertical axis of said collection chamber and adapted to receive and capable of holding an initial quantity of liquid therein, fluid passage means extending into said container in fluid communication with said collection and seal chambers, and means for connecting a tube to said passage means for connecting said passage means in fluid communication with a cavity of a patient to be drained, said passage means extending into said seal chamber such that all gas flowing from the cavity to said gas outlet means flows into said seal chamber and through the liquid therein before reaching said gas outlet means and liquid flowing from the cavity to said collection chamber flows over the upper side of said upper wall before flowing into said collection chamber during operation of the device.

2. The device of claim 1 wherein said fluid passage means has its lower end in said seal chamber below the level of said initial quantity of liquid.

3. The device of claim 2 wherein said opening is intersected by the vertical axis of said seal chamber.

4. The device of claim 3 wherein said passage means extends through said opening.

5. The device of claim 2 wherein said container has internal walls spaced from said side walls to allow liquid which overflows said seal chamber through said opening to flow axially between said internal walls and said side walls during operation of the device.

6. The device of claim 5 wherein the upper surface of said upper wall is concave and the lower surface of said bottom wall is convex to facilitate the flow of liquid from said seal chamber to said collection chamber.

7. The device of claim 6 wherein said first named container includes a lid closing the upper end thereof and having an opening therein, said passage means extends through said lid opening and has flange means thereon for closing said opening about said passage means, said lid having said gas outlet means thereon, and said lid opening being above and in aligned relation with said opening in said upper wall of said seal chamber, and cap means for holding said passage means and flange means in place on said lid.

8. The device of claim 7 wherein said lid and the interior walls of said collection chamber having means for locating said seal chamber.

9. The device of claim 1 wherein said seal chamber comprises a second container insertable into said first named container.

10. The device of claim 9 wherein said first named container includes a lid closing the upper end thereof and disposed above said seal chamber upper wall.

11. The device of claim 10 wherein said passage means extends through said lid and said upper wall.

12. The device of claim 11 wherein said opening is intersected by the vertical axis of said container.

13. The device of claim 11 wherein said gas outlet means is in said lid.

14. The device of claim 10 wherein said first named container and said lid include means for predeterminately locating said second container in said first named container.

15. The device of claim 1 wherein the length and width of said seal chamber is substantially greater than the height thereof, and said bottom wall, said side walls, and said upper wall are of substantially rigid plastic material.

16. The device of claim 1 wherein said collection and seal chambers are formed of a relatively rigid material.

17. The device of claim 16 wherein the length and width of said seal chamber are greater than the height thereof.

18. The device of claim 1 wherein said container has closure lid means at the upper end thereof and spaced above said seal chamber.

19. A fluid drainage device for collecting drainage fluid from a cavity of a patient comprising a relatively rigid container having a fluid drainage collection chamber therein, a liquid seal chamber therein having a bottom wall, side walls, an upper wall connected to the side walls above said bottom wall and extending generally radially inwardly from said side walls, and an opening in said upper wall connecting said collection and seal chambers in fluid communication, said container having lid means at the upper end thereof spaced above said seal chamber upper wall and defining with said upper wall a space interiorly of said container and in fluid communication with said collection chamber, gas outlet means for permitting removal of gas from the interior of said container, said seal chamber being disposed above said collection chamber in fluid communication therewith and adapted to receive and capable of containing an initial quantity of liquid therein, and fluid passage means extending through said lid and into said seal chamber for connection in fluid communication with a cavity of a patient to be drained and such that all gas flowing from the cavity into said outlet means flows into said seal chamber and through the liquid therein to said gas outlet means and substantially all liquid flowing from the cavity to said collection chamber flows over the upper side of said upper wall before flowing into said collection chamber during operation of the device.

20. The device of claim 19 wherein the vertical axis of symetry of said seal chamber is substantially coincident with that of said collection chamber.

21. The device of claim 19 wherein the length of said seal chamber is at least three times its height.

22. The device of claim 21 wherein the center of said opening is intersected by a vertical axis of said seal chamber, and the width of said seal chamber is greater than twice the diameter of said opening.

23. The device of claim 22 wherein the vertical axes of said collector and are substantially coincident, said seal chamber upper wall is of substantially rigid plastic and extends toward the center of said seal chamber and said passage means includes a tube extending through said upper wall with the lower end thereof spaced from said bottom wall, and said bottom wall is of substantially rigid plastic material.

24. A fluid drainage device for collecting drainage fluid from a cavity of a patient comprising a container having a fluid drainage collection chamber therein, a liquid seal chamber therein having a bottom wall, side walls, an upper wall extending generally radially inwardly from said side walls and spaced above said bottom wall, and an opening spaced from said bottom wall connecting said collection and seal chambers in fluid communication, gas outlet means for removing gas from the interior of said container, said seal chamber being disposed above said collection chamber with its vertical axis substantially coincident with the vertical axis of said collection chamber and adapted to receive an initial quantity of liquid therein, fluid passage means extending into said container in fluid communication with said collection and seal chambers with its lower end in said seal chamber below the level of said initial quantity of liquid and adapted for connection in fluid communication with a cavity of a patient to be drained so that all gas flowing from the cavity to said gas outlet means flows into said seal chamber and through the liquid therein before reaching said gas outlet means and liquid from the cavity flows over said upper wall and into said collection chamber during operation of the device, and indicia means on the device providing a visual indication of the level to which said seal chamber is to be filled by said initial quantity of liquid.

25. A fluid drainage device for collecting drainage fluid from a cavity of a patient comprising a container having a fluid drainage collection chamber therein, a liquid seal chamber therein having a bottom wall, side walls, an upper wall connected to the side walls above said bottom wall and extending generally radially inwardly from said side walls, and an opening spaced from said bottom wall connecting said collection and seal chambers in fluid communication, said container having lid means at the upper end thereof spaced above said seal chamber upper wall and defining with said upper wall a space interiorly of said container and in fluid communication with said collection chamber, gas outlet means for permitting removal of gas from the interior of said container, said seal chamber being disposed above said collection chamber in fluid communication therewith and adapted to receive and contain an initial quantity of liquid therein, and fluid passage means extending into said container in fluid communication with said collection and seal chambers and adapted for connection in fluid communication with a cavity of a patient to be drained so that all gas flowing from the cavity into said outlet means flows into said seal chamber and through the liquid therein to said gas outlet means and liquid from the cavity can flow into said collection chamber during operation of the device, said opening being located substantially on the vertical axis of said seal chamber and having a diameter substantially less than the length and width of said upper wall to minimize the flow of liquid out of said seal chamber upon limited tipping of the device, said container and all of the walls of said seal chamber being of relatively rigid substantially transparent plastic material.

* * * * *